United States Patent [19]

Almond et al.

[11] Patent Number: 5,631,290
[45] Date of Patent: May 20, 1997

[54] FATTY ACID SALT PESTICIDAL COMPOSITION

[75] Inventors: David S. Almond, Victoria; Diana L. Parker, Brentwood Bay, both of Canada

[73] Assignee: W. Neudorff GmbH, Emmerthal, Germany

[21] Appl. No.: 288,986

[22] Filed: Aug. 11, 1994

Related U.S. Application Data

[63] Continuation of Ser. No. 19,109, Feb. 18, 1993, abandoned.

[51] Int. Cl.$^6$ .......................... A01N 31/02; A01N 37/02; A01N 37/06; A01N 65/00
[52] U.S. Cl. .......................... 514/560; 514/557; 514/558; 514/724; 424/195.1
[58] Field of Search .................. 514/558, 560, 514/724, 739, 557; 424/195.1

[56] References Cited

U.S. PATENT DOCUMENTS

| | | | |
|---|---|---|---|
| 1,963,100 | 12/1934 | Salzberg et al. | 558/10 |
| 1,993,040 | 12/1935 | Salzberg et al. | 514/514 |
| 2,030,093 | 2/1936 | Bousquet et al. | 514/724 |
| 2,466,663 | 4/1949 | Russ et al. | 514/558 |
| 3,199,944 | 8/1965 | Gabor et al. | 504/313 |
| 3,236,626 | 2/1966 | Lindner | 71/DIG. 1 |
| 3,438,765 | 4/1969 | Tso et al. | 504/143 |
| 3,824,094 | 7/1974 | Tso et al. | 504/184 |
| 4,147,800 | 4/1979 | Singer et al. | 514/552 |
| 4,368,207 | 1/1983 | Lover et al. | 514/724 |
| 4,630,828 | 12/1986 | Smith et al. | 514/558 |
| 4,774,234 | 9/1988 | Puritch et al. | 514/560 |
| 4,826,678 | 5/1989 | Gaudet et al. | 424/93 L |
| 4,870,102 | 9/1989 | Puritch et al. | 514/560 |
| 4,983,591 | 1/1991 | Puritch et al. | 514/558 |
| 5,030,658 | 7/1991 | Salloum et al. | 514/560 |
| 5,047,424 | 9/1991 | Puritch et al. | 514/560 |
| 5,093,124 | 3/1992 | Kulenkampff | 424/195.1 |

OTHER PUBLICATIONS

"Use of Antitranspirant Epidermal Coatings for Plant Protection in China", Plant Disease, pp. 263–266, Apr. 1990.
"Journal Highlights", Plant Disease, pp. 263–266, Apr. 1990.
King, W.V. Chemicals Evaluated as Insecticides and Repellents at Orlando, fIA., Agriculture Handbook No. 69, US Dept of Agriculture, Washington, DC, 1954, pp. 11–13 and 105.
Stenius, P. et al., "Micelle formation and Phase equilibria of Surface–Active Components of Wood," Surfactants Solution [Proc. Int. Sym.], 4th, 1984, vol. 1, pp. 153–174.
Shah, D., "Significance of the 1:3 Molecular ratio in mixed Surfactant system," Journal of Colloid and Interface Science, vol. 37, No. 4, 1971, pp. 744–752.

*Primary Examiner*—John Pak
*Attorney, Agent, or Firm*—William C. Geary, III; Nutter, McClennen & Fish, LLP

[57] ABSTRACT

A non-phytotoxic, environmentally compatible composition provides improved efficacy against soft-bodied insects and mites. The composition comprises a fatty acid salt active ingredient and an adjuvant that surprisingly increases the spreadability and efficacy of the active ingredient. The active ingredient is a potassium, sodium, ammonium, or alkanolamine salt of one or a mixture of monocarboxylic fatty acids having from 8 to 22 carbon atoms. The adjuvant can be a fatty alcohol having from 4 to 18 carbon atoms, or a methyl or ethyl ester of fatty acids having from 4 to 18 carbon atoms. The ratio of the adjuvant to the active ingredient ranges from about 1:0.1 to 1:50.

4 Claims, No Drawings

FATTY ACID SALT PESTICIDAL COMPOSITION

This application is a continuation of application Ser. No. 08/019,109, filed on Feb. 18, 1993, now abandoned.

BACKGROUND OF THE INVENTION

The invention relates to pesticidal compositions, particularly those having insecticidal and miticidal activity, that are formed from environmentally safe compounds.

Fatty acids are naturally occurring, readily biodegradable compounds. The salts of certain fatty acids are known to have insecticidal and miticidal properties. Indeed, fatty acid salts having from 8 to 18 carbon atoms, particularly unsaturated C18 fatty acids, are toxic to many soft bodied insects.

Such insecticidal compounds are desirable because their biodegradability renders them ecologically safe compounds. However, fatty acid salt insecticides are acute toxins that exhibit no residual activity. To be effective as a pesticide these compounds must contact target pests. Factors which influence the effectiveness of such insecticides include the ability of the compound to effectively spread on a target surface and the ability of the compound to penetrate the insect's cuticle.

Various fatty acid-based pesticidal compositions are disclosed in U.S. Pat. Nos. 4,774,234; 4,826,678; and 5,093,124.

Fatty alcohols are not soluble in water, therefore these compounds are not effective for increasing spreading properties of water. Higher fatty alcohols have been reported to be active against aphids. (See Bosquet et al. Industrial and Engineering Chemistry, 27:1342–44 (1935). However, derivatives of fatty alcohols have been used more extensively than fatty alcohols themselves as pesticides. U.S. Pat. Nos. 1,993,040 and 1,963,100 disclose the use of higher alkyl thiocyanates, isothiocyanates, selenocyanates, isoselenocyanates, tellurocyanates, and isotellurocyanates in pesticidal formulations.

U.S. Pat. No. 3,199,944 discloses the use of long chain fatty alcohols as film formers able to be applied to bodies of water to inhibit evaporation. Similarly, Han (Plant Disease, April 1990, 263) discloses the use of a composition containing dodecyl alcohol to form a film or membrane over living plants. The membrane accommodates the passage of oxygen and carbon dioxide, but prevents the passage of water. Such a composition is reported to protect plants from insects, disease, cold, and dehydration.

Despite the known effectiveness of certain fatty acid-based compositions as pesticides, there is still a need for similar environmentally-compatible compositions that provide enhanced efficacy as well as ease and economy of manufacture.

SUMMARY OF THE INVENTION

It is accordingly an object of the invention to provide a fatty acid salt-based pesticidal composition having improved efficacy against a wide range of insects and mites. Another object is to provide an environmentally compatible pesticidal composition having enhanced activity. A further object is to provide a fatty acid salt-based pesticidal composition exhibiting improved handling characteristics and improved spreadability. Other objects will be apparent to one of ordinary skill in the art upon reading the disclosure that follows.

The invention relates to an environmentally safe insecticidal composition that is effective against a variety of insects and mites. The composition comprises a fatty acid salt-based active ingredient and an adjuvant to improve the spreadability of the fatty acid salt. The fatty acid salt preferably is a monovalent or polyvalent metal salt, or an organic salt of a fatty acid having from 8 to 22 carbon atoms. The active ingredient may comprise a single fatty acid salt or a fatty acid salt mixture such as coconut fatty acid salt or certain vegetable oil salts. The adjuvant preferably comprises a fatty alcohol having from 4 to 18 carbon atoms or a fatty acid ester having from 4 to 18 carbon atoms.

The fatty acid salt active ingredient may be present at a range of about 0.1 to 2.0. percent by weight. The ratio of the adjuvant to the fatty acid salt active ingredient ranges from about 1:0.1 to 1:50, and more preferably from about 1:10 to 1:50.

The composition may also include an organic solvent which may be a lower alcohol, a glycol or a vegetable or mineral oil.

Among the advantages of the pesticidal composition of the invention are its environmental compatability and its effectiveness against a variety of insects and mites. Moreover, the composition exhibits low phytotoxicity and may be applied directly to plants upon which the target pests are present.

In another aspect, the invention provides a method of controlling pests, such as insects and mites, through the use of the composition.

DETAILED DESCRIPTION OF THE INVENTION

The invention provides an environmentally-compatible, non-phytotoxic pesticidal composition effective against a variety of insects and mites. The composition comprises a fatty acid salt-based active ingredient and an adjuvant to enhance spreadability of the fatty acid salt. The fatty acid salt active ingredient comprises one or a mixture of fatty acid salts having from 8 to 22 carbon atoms. The salts preferably are monovalent metal salts, such as potassium and sodium, or ammonium salts of fatty acids. Other useful fatty acid salts include polyvalent metal salts and alkanolamine salts. Suitable polyvalent metal salts include the iron, calcium, and copper salts of fatty acids having from 8 to 22 carbon atoms. Suitable alkanolamine salts are the mono-, di-, and tri-ethanolamine salts of fatty acids having from 8 to 22 carbon atoms.

Among the most preferred fatty acid salt compounds are the potassium, sodium, and ammonium salts of oleic acid, linoleic acid, or linolenic acid.

Other preferred active ingredients include the sodium, potassium, and ammonium salts of coconut fatty acid. Coconut fatty acid, as is understood by those of ordinary skill in the art, is a mixture of various fatty acids. A typical fatty acid profile of coconut fatty acid is as follows:

| 7% caprylic acid | C8 |
| 6% capric acid | C10 |
| 48% lauric acid | C12 |
| 19% myristic acid | C14 |
| 9% palmitic acid | C16 |
| 2% stearic acid | C18 |
| 8% oleic acid | C18:1 |
| 1% linoleic acid | C18:2 |

Other useful active ingredients include salts of neem oil or various vegetable oils, including soybean oil salts, sunflower oil salts, canola oil salts, olive oil salts, and sesame oil salts.

Sodium, potassium and ammonium salts of these oils are among the most preferred.

Typical fatty acid profiles of such oils are as follows:

Sunflower Oil

| | | |
|---|---|---|
| 8% | palmitic acid | C16 |
| 3% | stearic acid | C18 |
| 0.5% | arachidic acid | C20 |
| 0.2% | behenic acid | C22 |
| 20% | oleic acid | C18:1 |
| 67.8% | linoleic acid | C18:2 |
| 0.5% | linolenic acid | C18:3 |

Canola Oil

| | | |
|---|---|---|
| 5% | palmitic acid | C16 |
| 2% | stearic acid | C18 |
| 63% | oleic acid | C18:1 |
| 20% | linoleic acid | C18:2 |
| 9% | linolenic acid | C18:3 |
| 1% | eicosenoic acid | C20:1 |

Olive Oil

| | | |
|---|---|---|
| 12% | palmitic acid | C16 |
| 2% | stearic acid | C18 |
| 0.5% | arachidic acid | C20 |
| 2% | palmitoleic acid | C16:1 |
| 70% | oleic acid acid | C18:1 |
| 13% | linoleic acid | C18:2 |
| 0.5% | linolenic acid | C18:3 |

Sesame Oil

| | | |
|---|---|---|
| 9% | palmitic acid | C16 |
| 5% | stearic acid | C18 |
| 42.5% | oleic acid | C18:1 |
| 43% | linoleic acid | C18:2 |
| 0.5% | linolenic acid | C18:3 |

Soybean Oil

| | | |
|---|---|---|
| 0.5% | lauric acid | C12 |
| 0.5% | myristic acid | C14 |
| 12% | palmitic acid | C16 |
| 25% | oleic acid | C18:1 |
| 52% | linoleic acid | C18:2 |
| 6% | linolenic acid | C18:3 |

Neem Oil

| | | |
|---|---|---|
| trace | myristic acid | C14 |
| 16% | palmitic acid | C16 |
| 18% | stearic acid | C18 |
| 2% | arachidic acid | C20 |
| 0.5% | behenic acid | C22 |
| 53% | oleic acid | C18:1 |
| 10.5% | linoleic acid | C18:2 |

The fatty acid salts that form the active ingredient of the pesticidal composition of the invention may be obtained commercially or may be formed by techniques well known in the art.

The concentration of the fatty acid salt can vary depending upon the needs of a given application. Generally, however, the fatty acid salt is present at a range of about 0.1 to 2.0 percent by weight of a ready-to-use composition. The composition, may, however, be formulated as a concentrate having about 50% by weight of the fatty acid salt active ingredient. The concentrate may be diluted with water before use to achieve a fatty acid salt concentration in the range of about 0.1 to 2.0 percent by weight.

The fatty acid salt active ingredient is known to be effective against insects and mites. However, these pesticides have no residual activity and thus must contact a target pest to be effective. It would thus be beneficial to increase the ability of the fatty acid salt active ingredient to spread over a target surface without increasing phytotoxicity of the composition and without jeopardizing the environmental compatability of the composition. Such an increase in the area covered by a given amount of the composition could increase the chances of contacting and killing a target pest. Intrinsic changes that increase spreadability could also increase the ability of compounds to penetrate the insect cuticle, trachae and spiracles, and thus improve efficacy.

Surprisingly, it has been found that fatty alcohols or fatty acid esters can be used as adjuvants to increase the spreadability of fatty acid salts. The use of such compounds yields a synergistic increase in the efficacy of the fatty acid salt. The fact that such compounds can serve as effective adjuvants is surprising because fatty alcohols are not soluble in water and cannot improve the spreading of water. Thus it is entirely unexpected that these compounds, when added to fatty acid salts, can increase the spreading and efficacy of the fatty acid salt. The unexpectedness of this discovery is highlighted by the fact that various surfactants, known to be good spreaders, did not increase the spreadabilty of the fatty acid salt active ingredient.

Fatty alcohols preferred for use with the invention include those having from 4 to 18 carbon atoms and, more preferably, those having from 10 to 14 carbon atoms. Among the most preferred fatty alcohols are decanol, undecanol, dodecanol, and tetradecanol. A preferred concentration range for these adjuvants, in a ready-to-use composition, is approximately 200 ppm (0.02% by wt.) to 2500 ppm (0.25% by wt.). The fatty alcohols can also be used at a higher concentration, (e.g., 0.25 to 2.0% by wt.).

Fatty acid esters preferred for use with the invention include methyl or ethyl esters of fatty acids having from 4 to 18 carbon atoms, and more preferably the methyl or ethyl esters of fatty acids having from 10 to 14 carbon atoms. Among the most preferred fatty esters are the methyl and, ethyl esters of capric acid, lauric acid, and myristic acid. One of ordinary skill in the art will understand that such fatty esters can be obtained commercially or prepared by the condensation reaction of the appropriate fatty acid with methanol or ethanol.

A preferred concentration range for the fatty alcohol and fatty ester adjuvants is 200 ppm (0.02% by wt.) to 2500 ppm (0.25% by wt.). Like fatty alcohols, fatty esters may also be present at a concentration equivalent to the fatty acid salts e.g., 0.1–2.0% by wt.).

The ratio of the adjuvant to the fatty acid salt may vary depending upon the intended use of the composition. Generally, it is preferred that this ratio be in the range of approximately 1:10 to 1:50. The adjuvant, as noted above, may also be present at a concentration range higher than that of the fatty acid salt such that the ratio of the adjuvant to the fatty acid salt is about 1:0.1. Such a composition, when applied to living plants, can act as an antitranspirant. Moreover, the composition can also control and provide protection against some plant diseases.

In one embodiment, a relatively small amount of a free fatty acid having from 2 to 22 carbon atoms can be used as an adjuvant. The free fatty acid can be present at less than 10 percent by weight of a concentrated formulation, and more preferably is present at about 3 to 5 percent by weight of a concentrated formulation.

The free fatty acid can be obtained commercially and incorporated into the formulation. One suitable fatty acid is oleic acid which may be obtained from a number of sources. Alternatively the free fatty acid can be obtained by only partially neutralizing the fatty acid salt present in the formulation. For example, in preparing the fatty acid salt by techniques well known to those of ordinary skill in the art, one could react an insufficient amount of base with the acid, thus leaving a desired amount of free fatty acid in the formulation. The free acid may also be obtained by adding a strong acid (e.g., hydrochloric acid, nitric acid, boric acid) to a fatty acid salt formulation to yield an appropriate amount of free fatty acid.

The composition may also include an organic solvent. Suitable solvents include lower alcohols (e.g., methanol, ethanol, and isopropanol), glycerol, ethylene glycol, propylene glycol, vegetable oil, and mineral oil. The solvent may be present in a concentrated formulation at a concentration range of about 30 to 45 percent by weight.

Generally, the composition can be prepared and stored in a concentrated formulation. Before use the concentrate is diluted with water to achieve the desired concentration of active ingredient. A preferred concentrate typically contains about 50 percent by weight of the active ingredient, 30 to 45 percent by weight of solvent, and 1 to 10 percent by weight of adjuvant. The balance of the concentrate can be made up of water.

Alternatively, the composition can be prepared by drying the fatty acid salt to powder form and combining the powder with the adjuvant (e.g., fatty alcohol). The composition can thus be formulated as a wettable powder or granule formulation.

In addition to providing increased efficacy, the pesticidal compositions of the invention are desirable as they exhibit low phytotoxicity. As a result, they are able to be applied directly to living plant tissue upon which insects and mites are present without damaging the plant.

The composition of the invention is effective against mites and against soft bodied insects, particularly those of the Order Homoptera (e.g., aphids, adelgids, leafhoppers, mealybags, psyllids, scales, and whitefly). The composition is also effective against species in other orders incuding Order Dermaptera (e.g., European earwig), Order Thysanoptea (e.g., thrips), Order Siphonaptera (e.g., fleas), Order Diptera (e.g., *fungas gnats*), Order Lepidoptera (e.g., tent caterpillars), Order Hymenoptera (e.g., rose slug), Order Orthoptera.(e.g., grasshoppers), Order Hemiptera (e.g., boxelder bug).

The following non-limiting examples serve to further describe the invention.

EXAMPLE 1

Summary of Spreading Results for a Potassium Oleate Formulation with Various Alcohols Concentrated potassium oleate formulations (50.0% active ingredient (ai)) were prepared and 4.0% of the appropriate fatty alcohol was added. Spreading was evaluated with samples diluted to 1.0% ai. Spreading was evaluated using a standardized parafilm assay. An Eppendorf pipettor dispensed 100 microliter of each sample onto a sheet of parafilm. The droplet was allowed to spread for 90 seconds and the droplet diameter was measured to determine the area covered. The data obtained are illustrated in Table 1.

TABLE 1

| Spreading of salt + various alcohols | mean area $(mm^2/\pi)$ |
|---|---|
| methanol + ai | 33.6 |
| ethanol + ai | 32.2 |
| propanol + ai | 32.5 |
| isopropanol + ai | 34.8 |
| butanol + ai | 31.4 |
| 2-methyl-butanol + ai | 34.2 |
| pentanol + ai | 33.4 |
| heptanol + ai | 39.0 |
| octanol + ai | 37.8 |
| nonanol + ai | 41.0 |
| decanol + ai | 41.8 |
| undecanol + ai | 50.6 |
| undecenyl alcohol + ai | 42.9 |
| dodecanol + ai | 58.1 |
| tetradecanol + ai | 50.4 |
| hexadecanol + ai | 33.6 |
| oleyl alcohol + ai | 40.3 |
| ai alone | 34.0 |

Example 2

Spreading of Potassium Coconate with Dodecanol

A concentrated potassium coconate formulation (50.0% ai) was prepared and 4.0% dodecanol was added. Spreading was evaluated with samples diluted to 1.0% ai. Spreading was evaluated using the standardized parafilm assay described in example 1, and the results obtained are illustrated in Table 2.

TABLE 2

| Sample | Mean Spreading Area $(mm^2/\pi)$ |
|---|---|
| potassium coconate alone | 25.50 |
| potassium coconate + dodecanol | 59.29 |
| distilled water | 11.90 |

EXAMPLE 3

Efficacy of Potassium Oleate ai with Decanol Against European Earwig, *Forficula auricularia*

European earwig adults, *F. auricularia*, were collected from the field for testing. For each replicate, five insects were placed in each 30 dram vial. Treatments were applied with hand-held trigger sprayers (approximately 3–5 ml per replicate) by spraying directly into vials. Vial contents were then emptied onto paper towel lined styrofoam plates to drain off excess solution. After treatment, insects were transferred into a filter paper lined petri plate which contained a piece of lettuce and a piece of nasturtium leaf. Mortality was assessed after 72 hours, and the data are illustrated in Table 3.

TABLE 3

| Treatment | Observed Mean % Mortality | Expected Mean % Mortality[1] |
| --- | --- | --- |
| 1. 0.5% ai | 45.0 | — |
| 2. 1.0% | 50.0 | — |
| 3. 1000 ppm decanol | 5.0 | — |
| 4. 0.5% ai + 1000 ppm decanol | 80.0 | 50.0 |
| 5. 1.0% ai +1000 ppm decanol | 92.5 | 55.0 |
| 6. dH$_2$O | 7.5 | — |

[1]Expected mean % mortality = sum of the observed mortalities for the two components alone.

EXAMPLE 4

Efficacy of Potassium Oleate Formulations with Higher Fatty Alcohols Against European Earwig *F. auricularia*

Adults earwigs, *F. auricularia*, were treated using the standardized acute bioassay described in example 3. Mortality was assessed after 48 hours, and the data are illustrated in Table 4.

TABLE 4

| Treatment | Observed Mean Mortality | Expected Mean % Mortality |
| --- | --- | --- |
| 0.5% ai alone | 40.0 | — |
| 1.0% ai alone | 45.0 | — |
| 0.1% decanol alone | 5.0 | — |
| 0.1% dodecanol alone | 2.5 | — |
| 0.1% tetradecanol alone | 0.0 | — |
| 0.5% ai + 0.1% decanol | 60.0 | 45.0 |
| 1.0% + 0.1% decanol | 87.5 | 50.0 |
| 1.0% + 0.1% dodecanol | 97.5 | 47.5 |
| 1.0% + 0.1% tetradecanol | 70.0 | 45.0 |

EXAMPLE 5

Efficacy of Potassium Oleate with Decanol and Dodecanol Against Variegated Cutworm Larvae, *Peridroma saucia* (Hbn.)

Variegated cutworm, *P. saucia*, were reared in the laboratory on artificial diet. Each replicate, consisting of five larvae (3rd instar), was transfered onto a styrofoam plate and treatments were applied with hand-held trigger sprayers (approximately 3–5 ml per replicate). After treatment, insects were transferred onto paper towel lined styrofoam plates to drain off excess soultion. Each larva was then placed into an individual cell of a 50 cell plastic tray. Each cell contained a small piece of artificial diet and trays were covered with plate glass. Mortality was assessed after 48 hours, and the data are illustrated in Table 5.

TABLE 5

| Treatment | Observed Mean % Mortality | Expected Mean % Mortality |
| --- | --- | --- |
| 0.5% ai | 87.5 | — |
| 0.1% decanol alone | 0.0 | — |
| 0.5% ai + 0.1% decanol | 92.5 | 87.5 |
| 0.5% ai alone | 72.5 | — |
| 0.1% dodecanol | 0.0 | — |
| 0.5% ai + 0.1% dodecanol | 92.5 | 72.5 |

EXAMPLE 6

Efficacy of Potassium Oleate with Various Fatty Alcohols Against Cutworm Larvae, *P. Saucia*

Variegated cutworm larvae (4th to 5th instar), *P. saucia*, were treated using the standardized acute bioassay described in example 5, and the data are illustrated in Table 6.

TABLE 6

| Treatment | Observed Mean % Mortality | Expected Mean % Mortality |
| --- | --- | --- |
| 0.5% ai | 7.5 | — |
| 0.1% tetradecanol alone | 2.5 | — |
| 0.5% ai + 0.1% tetradecanol | 22.5 | 10.0 |
| 0.1% hexadecanol alone | 2.5 | — |
| 0.5% ai + 0.1% hexadecanol | 17.5 | 10.0 |
| 0.1% 2-methyl-butanol | 0.0 | — |
| 0.5% ai + 0.1% 2-methyl-butanol | 27.5 | 7.5 |
| distilled water | 0.0 | — |

EXAMPLE 7

Efficacy of Potassium Oleate with Higher Fatty Alcohols Against Twospotted Spider Mite, *Tetranychus urticae* Koch Bush bean plants were cut back to two leaves each. A band of white petroleum jelly was applied at the base of the petioles (i.e., node) to contain mites on the leaves. Foliage covered with mites was obtained from a rearing facility and placed in plastic bags. Twenty-five adult female mites were transferred from the rim of the plastic bag, using a camel hair brush, to one leaf on each plant. Mite infested plants were left overnight and treatments were applied to wetting the next day (top and bottom leaf surfaces) using hand-held trigger sprayers. After treatment, plants were set out in a completely randomized block design on a lab bench. Mortality was assessed 24 hours after treatment, and the data are illustrated in Table 7.

TABLE 7

| Treatment | Observed Mean % Mortality | Expected Mean % Mortality |
| --- | --- | --- |
| 1.0% ai alone | 89.7 | — |
| 800 ppm dodecanol | 77.1 | — |

TABLE 7-continued

| Treatment | Observed Mean % Mortality | Expected Mean % Mortality |
| --- | --- | --- |
| 800 ppm tetradecanol | 56.8 | — |
| 800 ppm hexadecanol | 57.2 | — |
| 1.0% ai + 800 ppm dodecanol | 97.4 | 100.0 |
| 1.0% ai + 800 ppm tetradecanol | 99.2 | 100.0 |
| 1.0% ai + 800 ppm hexadecanol | 100.0 | 100.0 |
| distilled water | 16.3 | — |

EXAMPLE 8

Efficacy of Potassium Oleate with Decanol Against Cabbage Aphid, *Brevicorve brassicae* (L.)

Cabbage aphids, B, brassicae, were collected from the field and brushed onto plate glass for treatment. Each replicate, consisting of 10 aphids, were sprayed with one spray from a hand-held trigger sprayer. After one minute, treated aphids were transferred into filter paper lined petri plates using a fine camel hair brush. Mortality was assessed after 24 hours, and the data are illustrated in Table 8.

TABLE 8

| Treatment | Observed Mean % Mortality | Expected Mean % Mortality |
| --- | --- | --- |
| 0.5% al | 48.0 | — |
| 400 ppm decanol | 9.0 | — |
| 0.5% ai + 400 ppm decanol | 63.0 | 57.0 |
| distilled water | 14.0 | — |

EXAMPLE 9

Efficacy of Potassium Oleate with Decanol and Potassium Coconate with Dodecanol Against Cabbage Aphid, *B. brassicae*

Cabbage aphids, *B. brassicae* were treated using the standardized aphid plate glass bioassay described in example 8. The data are illustrated in Table 9.

TABLE 9

| Treatment | Observed Mean % Mortality | Expected Mean % Mortality |
| --- | --- | --- |
| 0.5% K+oleate ai alone | 52.0 | — |
| 400 ppm decanol alone | 6.0 | — |
| 0.5% K+ ai + 400 ppm decanol | 65.0 | 58.0 |
| 0.5% ai K+ coconate alone | 18.0 | — |
| 0.5% ai K+ coconate + 400 ppm dodecanol | 35.0 | 21.0 |
| 400 ppm dodecanol alone | 3.0 | — |

EXAMPLE 10

Efficacy of Dodecanol and Potassium Oleate Against Tobacco Aphids, *Myzus nicotianae* Blackman Tobacco aphids, *M. nicotianae*, were obtained from a rearing facility and treated using the standardized aphid plate glass bioassay described in Example 8, and the data are illustrated in Table 10.

TABLE 10

| Treatment | Observed Mean % Mortality | Expected Mean % Mortality |
| --- | --- | --- |
| 1.0% dodecanol | 34.0 | — |
| 0.1% ai | 4.0 | — |
| 1.0% dodecanol + 0.1% ai | 71.0 | 38.0 |
| 1.0% ai | 28.0 | — |
| 0.1% dodecanol | 2.0 | — |
| 1.0% ai + 0.1% dodecanol | 39.0 | 30.0 |
| distilled water | 1.0 | — |

Example 11

Spreading of Potassium Oleate Formulation with Esters

A concentrated potassium oleate formulation (50.0% ai) was prepared and 4.0% of the appropriate ester was added. Spreading was evaluated with samples diluted to 1.0% ai. Spreading was evaluated using the standardized parafilm assay described in example 1, and the data are illustrated in Table 11.

TABLE 11

| Formulation | Mean Area (mm2/π) |
| --- | --- |
| potassium oleate alone | 36.0 |
| potassium oleate + 4% methyl laurate | 40.3 |
| potassium oleate + 4% methyl caprate | 36.6 |
| potassium oleate + 4% ethyl caprate | 37.8 |

EXAMPLE 12

Efficacy of Potassium Oleate with Esters against Bean Aphid, *Aphis fabae* Scopoli Bean aphids, *A. fabae*, were treated using the standardized aphid plate glass bioassay described in example 8, and the data are illustrated in Table 12.

TABLE 12

| Treatment | Mean % Mortality |
| --- | --- |
| 1. 1.0% ai | 69.0 |
| 2. 1.0% ai w/800 ppm decanol | 88.0 |
| 3. 1.0% ai w/800 dodecanol | 86.0 |
| 4. 1.0% ai w/800 ppm methyl laurate | 88.0 |
| 5. 1.0% ai w/methyl caprate | 84.0 |
| 6. 1.0% ai w/800 ppm ethyl caprate | 87.0 |
| 7. dH$_2$O | 3.0 |

EXAMPLE 13

Efficacy of Potassium Sunflower Oil Salt with Dodecanol Against European Earwig, *Forficula auricularia* l.

European earwig adults, *F. auricularia*, were collected from the field for testing. For each replicate, five insects were placed in each 30 dram vial. Treatments were applied with hand-held trigger sprayers (ca. 3–5 ml per replicate) by spraying directly into vials. Vial contents were then emptied onto paper towel lined styrofoam plates to drain off excess solution. After treatment, insects were transferred into a filter paper lined petri plate which contained a piece of nasturtium leaf and a piece of nasturtium flower. Mortality was assessed after 72 hours and the data are illustrated in Table 13.

TABLE 13

| Treatment | Mean % Mortality |
| --- | --- |
| 1. 1.0% ai | 32.5 |
| 2. 1.0% ai + 800 ppm dodecanol | 62.5 |
| 3. dH$_2$O | 5.0 |

EXAMPLE 14

Efficacy of Potassium Olive Oil and Sunflower Oil Salts with Dodecanol Against Bean Aphid, *Aphis fabae* (Scopoli)

Bean aphids, *A. fabae*, were reared on nasturtium plants in the laboratory and brushed onto plate glass for treatment. Each replicate consisting of 10 aphids, were sprayed with one spray from a hand-held trigger sprayer. After one minute, treated aphids were transferred into filter paper lined petri plates using a fine camel hair brush. Mortality was assessed after 24 hours and the data are shown in Table 14.

TABLE 14

| Treatment | Mean % Mortality |
| --- | --- |
| 1. 1.0% ai K$^+$ olive oil salt | 52.0 |
| 2. 1.0% ai K$^+$ olive oil salt + 800 ppm dodecanol | 63.8 |
| 3. 1.0% ai K$^+$ sunflower oil soap | 48.0 |
| 4. 1.0% ai K$^+$ sunflower oil soap + 800 ppm dodecanol | 72.0 |
| 5. dH$_2$O | 8.0 |

EXAMPLE 15

Efficacy of Sodium/Potassium Sunflower Oil Salt with Dodecanol Against Bean Aphid, *A. fabae*

Bean aphids, *A. fabae*, were treated using the standardized aphid plate glass bioassay described in example 14. The data obtained are shown in Table 15.

TABLE 15

| Treatment | Mean % Mortality |
| --- | --- |
| 1. 1.0% ai Na$^+$/K$^+$ sunflower oil salt | 34.0 |
| 2. 1.0% ai Na+/K$^+$ sunflower oil soap + 800 ppm dodecanol | 65.0 |
| 3. dH$_2$O | 2.0 |

Example 16

Spreading of Potassium Oleate with Excess Fatty Acid.

Concentrated potassium oleate formulations (50% ai) were prepared with various amounts of KOH to produce salts with excess fatty acid (primarily oleic acid). Spreading was evaluated with samples diluted to 1.0% ai (salt+fatty acid). Spreading was evaluated using a standardized parafilm assay. An Eppendorf pipettor dispensed 100 microliter of each sample onto a piece of parafilm. The droplet was allowed to spread for 90 seconds and then the droplet diameter was measured to determine the area covered. The data is illustrated in Table 16.

TABLE 16

| Sample | Mean Spreading Area (mm$^2$/π) |
| --- | --- |
| potassium oleate - neutralized | 33.45 |
| potassium oleate - 3% excess fatty acid | 46.92 |
| potassium oleate - 5% excess fatty acid | 52.80 |
| potassium oleate - 10% excess fatty acid | 52.32 |
| potassium oleate - 15% excess fatty acid | 49.23 |
| potassium oleate - 20% excess fatty acid | 51.12 |
| potassium oleate - 25% excess fatty acid | 50.65 |

Example 17

Efficacy of Potassium Oleate with Excess Fatty Acid Against Bean Aphid, *A. fabae*

Bean aphids, *A. fabae*, were treated using the standardized aphid plate glass bioassay described in example 14. For each replicate, aphids were transferred into filter paper lined petri plates after exposure to treatments for 75 seconds. The data are illustrated in Table 17.

TABLE 17

| Treatment | Mean % Mortality |
| --- | --- |
| 1. Potassium oleate - neutralized | 21.0 |
| 2. Potassium oleate - 3% excess fatty acid | 53.0 |
| 3. Potassium oleate - 5% excess fatty acid | 54.0 |
| 4. Potassium oleate - 10% excess fatty acid | 43.0 |
| 5. dH$_2$O | 2.0 |

Example 18

Efficacy of a Diethanolamine Salt of Oleic Acid with Dodecanol Against Bean Aphid, *A. fabae*

Bean aphids, A. fabae, were treated using the standardized aphid plate glass bioassay described in example 14. For each replicate, aphids were transferred into filter paper lined petri plates after exposure to treatments for 75 seconds. The data are illustrated in Table 8.

TABLE 18

| Treatment | Observed Mean % Mortality | Expected Mean % Mortality |
|---|---|---|
| 1. 1.0% ai | 50.0 | — |
| 2. 800 ppm dodecanol | 1.0 | — |
| 3. 1.0% ai + 800 ppm dodecanol | 62.0 | 51.0 |
| 4. dH$_2$O | 3.0 | — |

It is understood that various modifications may be made to the invention described herein without departing from the intended scope of the claims.

What is claimed is:

1. An environmentally compatible composition toxic to insects, consisting essentially of
   an insecticidally effective amount of an active ingredient selected from the group consisting of sodium salt of oleic acid, potassium salt of oleic acid, ammonium salt of oleic acid, sodium salt of sunflower oil, potassium salt of sunflower oil, ammonium salt of sunflower oil, sodium salt of canola oil, potassium salt of canola oil, ammonium salt of canola oil, sodium salt of sesame oil, potassium salt of sesame oil, ammonium salt of sesame oil, sodium salt of olive oil, potassium salt of olive oil, and ammonium salt of olive oil, present at 0.1 to 2.0 percent by weight;
   a solvent component selected from the group consisting of water, lower alcohols, glycerol, ethylene glycol, vegetable oil, and mineral oil; and
   an adjuvant, present at 0.02 to 0.1% by weight to increase the spreadability and efficacy of the active ingredient, the adjuvant selected from the group consisting of decanol, dodecanol and tetradecanol,
   the ratio of the adjuvant to the fatty acid salt being in the range of about 1:2 to 1:50, and the composition having the property of being non-phytotoxic.

2. The composition of claim 1 wherein the ratio of the adjuvant to the active ingredient is in the range of about 1:10 to 1:50.

3. An environmentally compatible composition toxic to insects, consisting essentially of, in a ready-to-use formulation:
   an insecticidally effective amount of an active ingredient selected from the group consisting of sodium salt of oleic acid, potassium salt of oleic acid, ammonium salt of oleic acid, sodium salt of sunflower oil, potassium salt of sunflower oil, ammonium salt of sunflower oil, sodium salt of canola oil, potassium salt of canola oil, ammonium salt of canola oil, sodium salt of sesame oil, potassium salt of sesame oil, ammonium salt of sesame oil, sodium salt of olive oil, potassium salt of olive oil, and ammonium salt of olive oil, present at 0.1 to 2.0 percent by weight; and
   an adjuvant selected from the group consisting of decanol, dodecanol and tetradecanol, the adjuvant being present ar a concentration ranging from about 0.02 to 0.1% by weight.

4. A method of killing insects on a surface, comprising:
   providing a non-phytotoxic composition consisting essentially of (1) an active ingredient selected from the group consisting of sodium salt of oleic acid, potassium salt of oleic acid, ammonium salt of oleic acid, sodium salt of sunflower oil, potassium salt of sunflower oil, ammonium salt of sunflower oil, sodium salt of canola oil, potassium salt of canola oil, ammonium salt of canola oil, sodium salt of sesame oil, potassium salt of sesame oil, ammonium salt of sesame oil, sodium salt of olive oil, potassium salt of olive oil, and ammonium salt of olive oil, present at, about 0.1 to 2.0% by weight of the composition, and (2) an adjuvant selected from the group consisting of decanol, dodecanol and metradecanol, the adjuvant being present at a concentration in the range of about 0.02 to 0.1% by weight of the composition; and
   applying an insecticidally effective amount of the composition to insects or to surfaces infested by insects.

* * * * *